(12) United States Patent
Alanazi et al.

(10) Patent No.: US 8,647,674 B2
(45) Date of Patent: Feb. 11, 2014

(54) USE OF DATE SYRUP AS A BINDER

(75) Inventors: Fars Kaed M. Alanazi, Riyadh (SA); Ibrahim Abdullah Ibrahim Alsarra, Riyadh (SA); Diaa Eldin Zidan Zidan Shaaban, Riyadh (SA)

(73) Assignee: King Saud University, Riyadh (SA)

( * ) Notice: Subject to any disclaimer, the term of this patent is extended or adjusted under 35 U.S.C. 154(b) by 15 days.

(21) Appl. No.: 13/259,725

(22) PCT Filed: Mar. 25, 2010

(86) PCT No.: PCT/EP2010/001885
§ 371 (c)(1),
(2), (4) Date: Nov. 3, 2011

(87) PCT Pub. No.: WO2010/108683
PCT Pub. Date: Sep. 30, 2010

(65) Prior Publication Data
US 2012/0040023 A1    Feb. 16, 2012

(30) Foreign Application Priority Data
Mar. 25, 2009  (SA) .................................. 109300197

(51) Int. Cl.
*A61K 9/16*    (2006.01)

(52) U.S. Cl.
USPC ........................... 424/489; 424/439; 424/686

(58) Field of Classification Search
None
See application file for complete search history.

(56) References Cited

U.S. PATENT DOCUMENTS

2005/0281876 A1* 12/2005 Li et al. .......................... 424/473

FOREIGN PATENT DOCUMENTS

WO    WO 2007/107787    9/2007

OTHER PUBLICATIONS

Wikipedia "Calcium Bicarbonate" (pp. 1-2; retrieved online on Jan. 18, 2013) (http://en.wikipedia.org/wiki/Calcium_bicarbonate).*
Wikipedia Calcium Carbonate (pp. 1-11; retrieved online on Jan. 18, 2013) (http://en.wikipedia.org/wiki/Calcium_carbonate).*
"Date Syrup" pp. 1-2, Jun. 9, 2008; (http://goneraw.com/recipe/date-syrup-1).*
"Homemade Raw Vegan Date Syrup Recipe" pp. 1-2, retrieved online on May 16, 2013; (http://www.greenthickies.com/date-syrup).*
"Date Palm Products" Chapter 3: Derived Date Fruit Products by Barreveld, FAO agricultural services bulletin No. 101 (FAO Coporation Document Repository from FAO of the United Nations), Book, 1993, p. 1-19 (http://www.fao.org/docrep/t0681e/t0681e07.htm).*
Al-Farsi, Clarification of date juice, *International Journal of Food Science and Technology*, Mar. 2003, vol. 38, No. 3 pp. 241-245, XP-002585216.
Anonymous, Shabnam 7000: Date, *Shabnam 7000*, Dec. 2008, XP-002585215, http://www.shabnam7000.com/en/category/date_sh/.
Aldhaheri et al., "Chemical composition of date pits and reproductive hormonal status of rats fed date pits", *Food Chemistry*, 2004, vol. 86, pp. 93-97.
Al-Gboori et al., "Importance of Date Palms as a Source of Nutrition", *Agricultura Tropica et Subtropica*, 2010, vol. 43, No. 4, pp. 341-347.
Al-Hooti et al., "Chemical composition and quality of date syrup as affected by pectinase/cellulose enzyme treatment", *Food Chemistry*, 2002, vol. 79, pp. 215-220.
Al-Mamaryet al., "The in vitro antioxidant activity of different types of palm dates (*Phoenix dactylifera*) syrups", *Arabian Journal of Chemistry*, 2011, doi:10.1016/j.arabjc.2010.11.014.

* cited by examiner

*Primary Examiner* — Bethany Barham
(74) *Attorney, Agent, or Firm* — Saliwanchik, Lloyd & Eisenschenk

(57) ABSTRACT

This invention is concerned with the use of date syrup used as a binder (agglutinant) for solid dosage forms, such as tablets. The features of the granules and the tablets have been studied in comparison with granules and tablets which use different types of agglutinants such as starch paste and sucrose syrup and the results have shown that the use of date syrup as a binder for tablets yields results superior to other kinds of binders. In addition, date syrups gives the granules and tablets a fair color, good taste, distinct and pleasant odor, and it is favorable in regards to shape and taste by patients.

18 Claims, 3 Drawing Sheets

USE OF DATE SYRUP AS A BINDER

CROSS REFERENCE TO A RELATED APPLICATION

Figure 1:
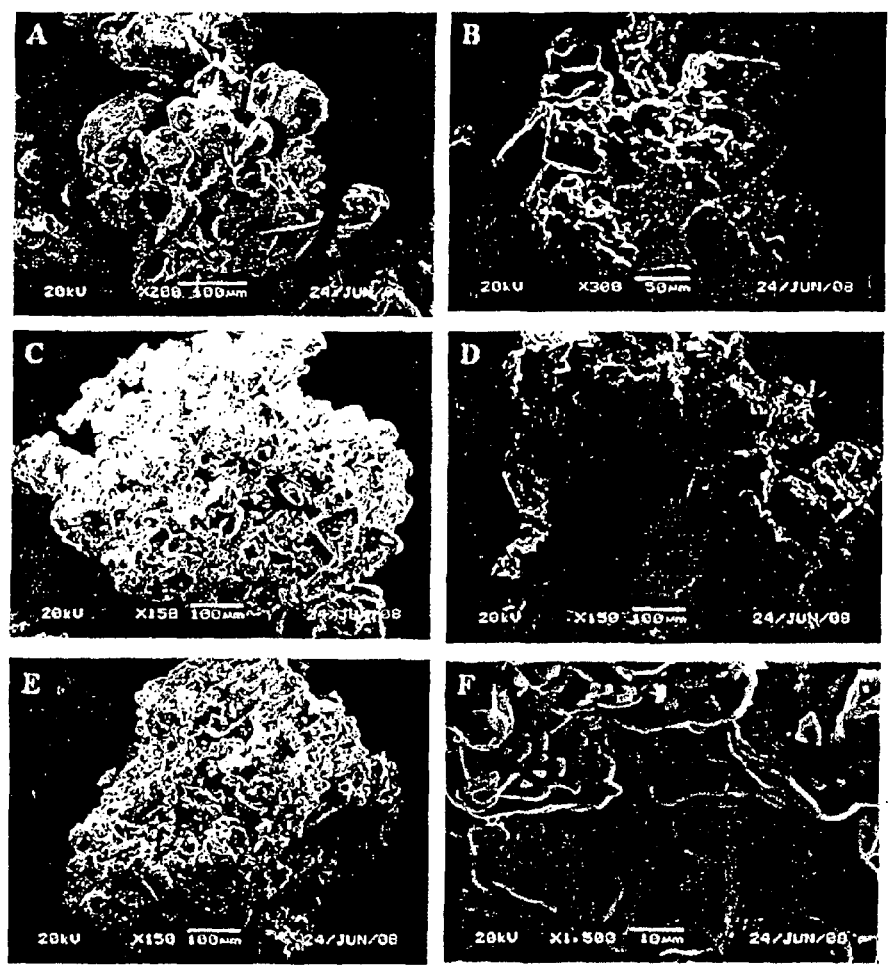

This application is a National Stage Application of International Application Number PCT/EP2010/001885, filed Mar. 25, 2010; which claims priority to Saudi Arabia Application No. 109300197, filed Mar. 25, 2009; all of which are incorporated herein by reference in their entirety.

The present invention relates to the use of date syrup as an agglutinant. Moreover, the present invention relates to a method of producing a solid dosage form using date syrup. Furthermore, the present invention relates to a solid dosage form comprising date syrup as an agglutinant.

This invention is about using date syrup as agglutinant, since most powders cannot be directly pressed into tablets because of its small particles which make it lack the appropriate qualities to make it stick and bind together to form a compressed shape. Granulation is used to reduce the size of the particles in these powders so that it will become compressible with the use of binders which are substances that help particles stick together.

Typically, these binders are either sugars or polymers while the date syrup that is used according to the present invention has now been found by the present inventors to be a granulation agent for both substances that are soluble and insoluble in water. In addition, it has the ability to mask the taste given its distinct flavor and gives a fair taste.

Date syrup is dark brown drink extracted from palm dates and contains sugars that reach up to 88% and most of the sugar is glucose and fruit sugar. In addition, date syrup contains substances with nutritional value and is considered a high source for potassium, magnesium, and calcium.

Classical binders or tablet agglutinants are typically polymers or sugars and may only be used to granulate only water-soluble substances or, alternatively, water-insoluble substances. Accordingly, it was an object of the present invention to provide for an alternative agglutinant. Moreover, it was an object of the present invention to provide for an agglutinant that is capable of granulating both water-soluble substances as well as water-insoluble substances at the same time.

All these objects are solved by the use of date syrup as an agglutinant for granulation of water-soluble substances such as sodium-bicarbonate and of water-insoluble substances, such as calcium carbonate. In one embodiment, said use is for manufacturing of solid dosage form.

In one embodiment, said date syrup is used at a concentration in the range of from 40% to 60%, preferably 40%, 50% or 60%.

In one embodiment, the agglutinant is an agglutinant for a solid dosage form selected from tablets, pills, lozenges, capsules, suppositories, powders, granules.

In one embodiment, said date syrup is used as agglutinant in an agglutinant solution, and the specific gravity, viscosity and/or pH value of said agglutinant solution is defined, wherein the specific gravity is 0.8-1.3 g/ml, and/or the viscosity is 4-20 cP, and/or the pH value is in a range of from 3-5, preferably 4-5.

In one embodiment, said water-soluble substances and said water-insoluble substances are assessed by their average molecular size, apparent density, pitting density and rest angle.

In one embodiment, said water-soluble substances and water-insoluble substances are granulized separately using date syrup, starch paste and sucrose syrup as different tablet agglutinants, such that granules and tablets are prepared.

In one embodiment, the shape and structure of the granules and tablets of said water-soluble and water-insoluble substances prepared with different tablet agglutinants, are studied using an electron microscope.

In one embodiment, the obtained granules of said substances are assessed according to their average molecular size, strength of the molecule, apparent density, pitting density and rest angle.

In one embodiment, tablets are manufactured from the granules prepared, using a tablet machine.

In one embodiment, the manufactured tablets are assessed and studied according to the American Pharmaceutical Constitution, Article 22, in relation to weight symmetry, time of disintegration, fragility test, and hardness test.

In one embodiment, the taste and flavor of the tablets manufactured is tested on a sample of volunteers.

The objects of the present invention are also solved by a solid dosage form, comprising date syrup as an agglutinant.

In one embodiment, the dosage form according to the present invention is selected from the group comprising tablets, pills, lozenges, capsules, suppositories, powders and granules.

In one embodiment, said dosage form has been prepared using the method in accordance with the present invention.

As used herein, the term "agglutinant" is meant to refer to a substance that allows a granulation of a powder. The term is used interchangeably herein with "binder" and/or "excipient".

Unless indicated otherwise herein, concentrations which are given as percentage values are weight/weight-percentages. In preferred embodiments, the date syrup is diluted with water so as to obtain concentrations of date syrup in water in the range of from 40 to 60% (w/w date syrup:water).

The objects of the present invention are also solved by a method of producing a solid dosage form, said method comprising:

providing the substance to be granulated, and mixing it with date syrup as an agglutinant, and blending the mixture thus obtained.

In one embodiment, further ingredients may be added, such as lubricants, agents influencing the release profile, further binder substances, humectants, etc.

The date syrup is as defined further above. It should be emphasized that date syrup and its composition will not change despite being derived from different origins. This is because the main components of the date syrup and the reduced sugars and transformed sugars which make 60 to 65 weight percent or more of the composition do not change at all. Consequently, a date syrup having a concentration of 40% (w/w date syrup:water) will be the same, regardless of the origin of the dates.

In one embodiment, the date syrup in accordance with the present invention has a specific gravity of 0.8-1.3 g/ml. In one embodiment, the date syrup in accordance with the present invention has a viscosity of 4-20 cP. In one embodiment, the date syrup in accordance with the present invention has a pH-value in the range of from 3 to 5, preferably 4 to 5. Date syrup, in accordance with the present invention, can be used for any solid dosage form known in the art. Examples thereof are, without being limited thereto: tablets, pills, lozenges, capsules, suppositories, powders and granules.

In accordance with the present invention, the use of date syrup as an agglutinant for solid dosage forms has the advantage that it shows superiority with respect to other conventional agglutinants, such as starch or sucrose syrup. Moreover, the production of date syrup is ecologically sustainable. The date syrup allows a granulation of both water-soluble and water-insoluble substances. Solid dosage forms, such as tablets, which have been produced using date syrup, are well received by patients. Solid dosage forms according to the present invention, in particular granules, show a number of advantageous qualities, including friability, hardness and uniformity.

In one embodiment, the use in accordance with the present invention comprises the following steps:

Providing a substance to be granulated and mixing it with date syrup. In one embodiment, the thus resultant mixture is subsequently blended. Optionally, further ingredients, such as other excipients, lubricants, humectants or further pharmaceutical ingredients may also be added. In one embodiment, the granules resultant from the afore-mentioned process are subsequently compressed to form tablets or pills or lozenges or other solid dosage forms. Such solid dosage forms may additionally and subsequently become coated.

In the following, reference is made to specific embodiments which are given to illustrate, not to limit the present invention.

In one embodiment, date syrup was used (solutions with concentrations 40, 50, and 60% date syrup:water) to granulize sodium-bicarbonates powders (soluble in water) and calcium-carbonate (insoluble in water) and also, other common binders were used such as starch paste (10% starch:water) and sucrose syrup (50% sucrose:water) to granulize the same powders and then produce tablets from the granules obtained. And, with the study of the resulting tablets, it was found that date syrup as a tablet binder yields results superior to both sucrose and starch paste.

BRIEF DESCRIPTION OF FIGURES AND TABLES

1—FIG. 1: Electronic microscope images of sodium bicarbonate granules prepared with different binders.

Figure 2:
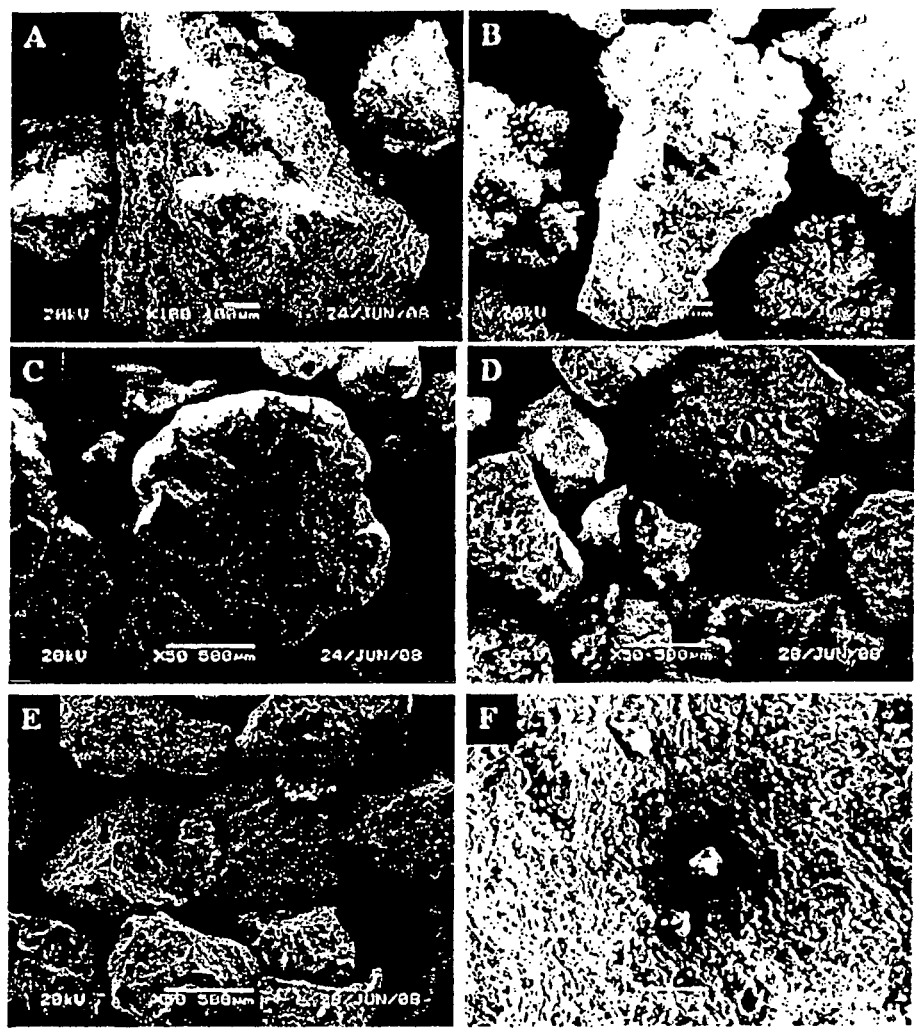

2—FIG. 2: Electronic microscope images of calcium carbonate granules prepared with different binders.

Figure 3:
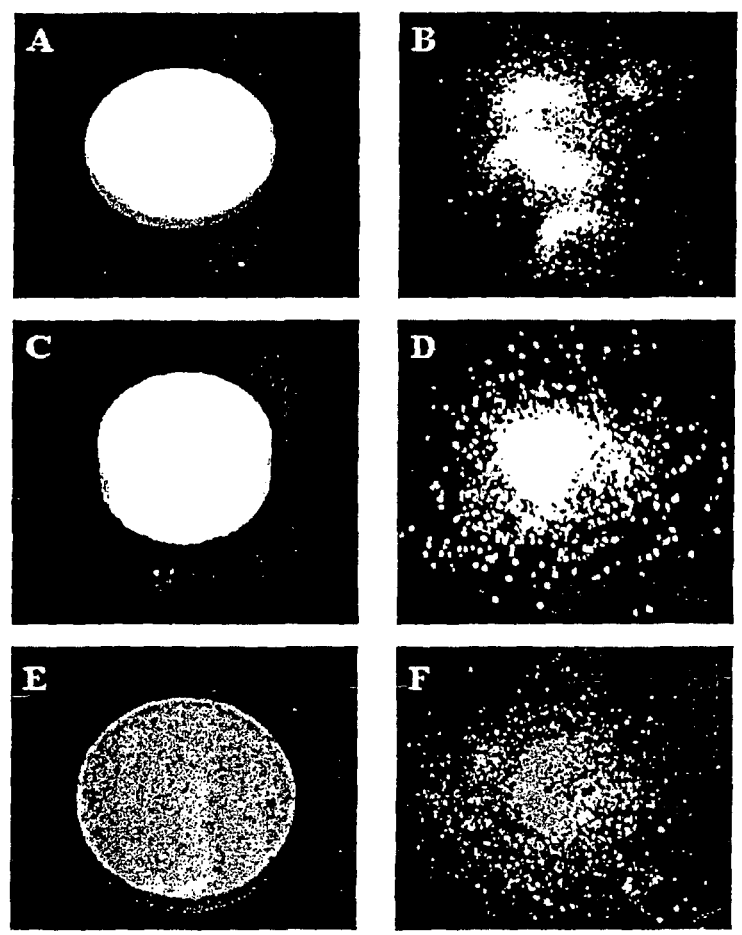

3—FIG. 3: Images of granules and tablets of sodium bicarbonates prepared with different binders.

4—Table 1: Contents of date syrup.

5—Table 2: Concentrations and quantities of the different binders used in granulating 750 gm of sodium bicarbonates and calcium carbonates.

6—Table 3: Elemental analysis of the date syrup used.

7—Table 4: Specific gravity, viscosity, and pH values of the dilute solutions of the different binders used.

8—Table 5: Features of sodium bicarbonates powders and calcium carbonate powders.

9—Table 6: Features of calcium carbonates granules.

10—Table 7: Features of sodium bicarbonates granules.

11—Table 8: Features of calcium carbonates tablets.

12—Table 9: Features of sodium bicarbonates tablets.

13—Table 10: Tablet sensation test.

DETAILED DESCRIPTION AND EXAMPLES

Elemental Analysis of Date Syrup:

The used Date syrup extracted from Al Ahssa area palm trees has been analyzed (Table 1), and which contains common binders as shown in Table (2), in the King Saud Center for Soil Research an Inductive Coupled Plasma Atomic Emission instrument (ICP-AE) and the main components, as shown in Table (3) has shown the special qualities that make date syrup superior to, as a tablet binder, other common binders.

Binder Preparation Methods:

a) Preparing date syrup solutions:

Date syrup solution diluted with water to obtain concentrations 40%, 50%, 60% (w/w date syrup:water).

b) Preparing starch paste (w/w starch:water):

The estimated amount of starch is suspended in an equal amount of water, and then the rest of the remaining water amount is added, boiling, and stirred until paste is formed.

c) Preparing sucrose syrup:

The estimated amount of sucrose is stirred in the estimated amount of warm water until it completely dissolves.

TABLE 1

| Components | Value |
|---|---|
| Moisture content (%) | 16 |
| Ash content (%) | 6.8 |
| Total solids on dry weight (%) | 84 |
| Total sugar (%) | 79.45 |
| Reduced sugar (%) | 4.87 |
| Invert sugar (%) | 74.83 |
| Total proteins (as N) (%) | 0.83 |
| Total lipids (fats) (%) | 1.98 |
| Pectin content (as calcium pectate) (%) | 1.46 |
| Vit. C. content (mg/100 g) | 0.185 |
| Minerals (mg/100 g) | |
| Sodium | 13 |
| Potassium | 202.8 |
| Iron | 7.8 |
| Magnesium | 143 |
| Calcium | 338 |

Determining the Specific Gravity, Viscosity, and pH Value for the Binder Solutions:

The viscosities of the date syrup, sucrose syrup and starch paste were measured using a Vibro Viscometer, the average of 3 readings were taken. The specific gravity was measured by taking the average of 5 samples (1 ml for each sample. The pH value was also measured for each (Table 4). The table shows similarity between date syrup, sucrose syrup and starch paste with regard to specific gravity. In regards to viscosity, starch paste gave the highest value (more than 12 times). The relation between the concentration of date syrup and viscosity gave a linear line with a high connection value ($r^2=0.945$). The fluid flow qualities of date syrups appear as if it is either a false flow flexibility or a dual flexibility besides the high negative value (−19) of the section indicate a production value 32.33 and this is explained with the date particles being in a flexible suspender and/or the existence of natural date syrup solutions (false flexibility flow). pH values have shown that the date syrup is a low acid such that the pH values range from 4.67 to 4.5 in comparison with sucrose syrup which gave a value of 5.7. This is due to the composition of the natural date syrup of sugars. pH values have an important role in the assessment of binders that play a role in the specific environment of pH around the soluble particles.

TABLE 2

| Formula No | Materials Name | Weight | Binders Name | Concentration % | Quantity of binder (g) |
|---|---|---|---|---|---|
| C1 | Calcium carbonate | 750 g | Starch | 10 | 487.5 |
| C2 | | | Sucrose | 50 | 450 |
| C3 | | | DS 40% * | 40 | 348.75 |
| C4 | | | DS 50% | 50 | 369.38 |
| C5 | | | DS 60% | 60 | 367.5 |
| N1 | Sodium bicarbonate | 750 g | starch | 10 | 123.75 |
| N2 | | | sucrose | 50 | 150 |
| N3 | | | DS 40% | 40 | 133.13 |
| N4 | | | DS 50% | 50 | 125.63 |
| N5 | | | DS 60% | 60 | 121.88 |

* DS = dates syrup

TABLE 3

| Constituents | Contents in mg/100 gm |
|---|---|
| Ca | 345.1 ± 10 |
| Cd | — |
| Cu | 0.34 ± 0.01 |
| Fe | 6.6 ± 0.36 |
| Mg | 138.8 ± 8 |
| Mn | 0.203 ± 0.01 |
| P | — |
| Pb | 0.26 ± 0.01 |
| Zn | 104.1 ± 6.8 |
| K | 194 ± 11 |

TABLE 4

| Binder | Specific gravity * (g/ml) | Viscosity * (CP) | pH Value |
|---|---|---|---|
| Starch (10%) | 1.096 ± 0.0005 | 202.3 ± 4.163 | — |
| Sucrose (50%) | 1.112 ± 0.0080 | 16.13 ± 0.208 | 5.7 |
| Dates syrup (40%) | 1.03 ± 0.0014 | 5.517 ± 0.424 | 4.67 |
| Dates syrup (50%) | 1.081 ± 0.0011 | 9.07 ± 0.845 | 4.59 |
| Dates syrup (60%) | 1.112 ± 0.0066 | 17.7 ± 0.265 | 4.55 |

* The means are calculated from at least of three determinations.
All reading results presented as mean ± S.D.
— means is not available Evaluating Sodium Bicarbonates and Calcium Carbonates Powders:

The average size of the particle was measured; apparent density, tapped density, and the rest angle for each powder (Table 5). It was revealed that each two substances suffer from having a small particle size, low, low apparent and tapped density which makes it impressible and these features are enhanced with the granulation process.

TABLE 5

| Parameter | Calcium Carbonate | Sodium bicarbonate |
|---|---|---|
| Mean particle size, μm | <63 | <63 |
| Angle of repose, ø ± S.D | 53 ± 5 | 55 ± 4 |
| Bulk density, $V_B$ · g/cm$^3$ ± S.D | 0.330 ± .012 | 0.503 ± 0.022 |
| Tapped density, $V_T$ · g/cm$^3$ ± S.D | 0.570 ± .030 | 1.001 ± 0.051 |
| Carr's Index, I | 42.1 | 49.7 |

* The means are calculated from at least of three determinations

Preparing the Granules:

Granulation was done by using a planetary blender (Erekwa-Apparatebau) with speed of 30 rotations/sec. Binders were added gradually to the solutions until cohesive dough was formed. The dough was then passed through a sieve (10 slots) and then dried in the oven at a temperature of 40° Celsius for 24 hours. The granules were then passed through a sieve (20 slots).

Study of the Composition and Shape (Morphology) of the Sodium Bicarbonates Granules and the Calcium Carbonates Granules Prepared with the Help of Different Binders, Using an Electronic Microscope (FIGS. 1 & 2):

The morphology of the granules and the shape of the binder plays an important role in the pharmaceutical and vital performance of the granules and tablets. The sodium bicarbonates granules appeared as particles joint together to form a granular composition composed of large particles (sodium bicarbonates) and small particles (binders). This applies to the starch paste and the sucrose syrup by the used concentrations (FIGS. 1a, b). In the case of the date syrup, the granules appeared as large particles enclosed in the binder (the date syrup) and became visible when increasing the concentration of the date syrups solution from 40 to 60% (FIGS. 1c, 1d, 1e). In the case of calcium carbonates granules, no apparent effect was observed of the binder types to the granular morphology of the granules due to their existence as a sole granular composition and could be due to the insoluble nature of calcium carbonates in water (FIGS. 2a, 2e).

Characteristics of the Calcium Carbonates Granules (Table 6):

Granulation led to the enhancement of the physical characteristics of the calcium carbonates and this was in particular the case when date syrup was used. The average size of particle was measured as well as the apparent density, tapped density, and the rest angle of the calcium carbonates granules. Granules prepared with date syrup yielded average particle size higher than that of sucrose syrup and starch paste. Granules prepared with starch paste yielded lowest average particle size and this reflects the high efficacy of date syrup as a binder and low efficacy for the starch paste. Date syrup produced granules with better uniformity as it was apparent from the rest angle results when compared with granules prepared with starch paste and sucrose syrup.

Based on frailty values, calcium carbonates granules prepared with date syrup show a better granule strength amongst the studied granules. Strong granules are helpful for the upcoming steps in the production method such as final blending and transferring because fragile granules has a bad effect on the specific uniformity and can cause dissolution of the blend. Humidity content was low (less than 1%) for different granules. Apparent density, tapped density and Kar indicator have shown characteristics lower than the level of the calcium carbonates prepared with starch paste especially if we observe the difference between apparent density and tapped density, and this is related to the weakness of the particle while date syrup and sucrose syrup gave similar results.

TABLE 6

| Binder | Particle size (μm) | Ø | Bulk density (g/cm³) | Tapped density (g/cm³) | Carr's Index | Moisture content (%) | Friability (%) |
|---|---|---|---|---|---|---|---|
| Starch paste | 519.3 | 34.62 ± 0.33 | 0.709 ± 0.025 | 0.797 ± 0.024 | 11.01 ± 1.12 | 0.63% | 1.44 ± 0.24 |
| Sucrose | 549.2 | 34.44 ± 0.65 | 0.757 ± 0.030 | 0.826 ± 0.027 | 8.38 ± 1.20 | 0.59% | 1.41 ± 0.27 |
| DS 40% | 614.5 | 33.4 ± 0.18 | 0.892 ± 0.030 | 0.928 ± 0.016 | 3.92 ± 1.55 | 0.40% | 1.22 ± 0.05 |
| DS 50% | 608.4 | 33.8 ± 0.29 | 0.874 ± 0.015 | 0.928 ± 0.016 | 5.83 ± 0.10 | 0.74% | 0.66 ± 0.21 |
| DS 60% | 610.9 | 32.87 ± 0.78 | 0.958 ± 0.036 | 1.001 ± 0.033 | 4.24 ± 1.75 | 0.46% | 1.23 ± 0.47 |

The results of angle of repose, moisture content and bulk density are the means of three determinations
Ø = Angle of repose (mean ± S.D.)

Characteristics of the Sodium Bicarbonates:

Granulation has enhanced the physical characteristic of the sodium bicarbonates powder. Using date syrup gave the largest particle size indicating high binding efficacy. Date syrup and sucrose syrup gave similar values of the rest angle indicating similar uniformity. Starch paste gave the highest rest angle value and weak uniformity (Table 7). Based on the frailty results, date syrup granules that has strong granular toughness while starch paste gave low value followed by sucrose syrup. Humidity content was low (less than 1%) for the different granules.

strength as revealed by the press strength (toughness) test. Starch paste produced tablets with the least press strength (toughness). Calcium carbonates tablets granulized with starch paste and calcium carbonates tablets granulized with sucrose syrup gave the longest disintegration time while tablets granulized with date syrup gave the shortest disintegration time and that is because disintegration of tablets depends on many factors of which are: press strength, mechanism of tablet, solubility in water, nature of the binder, and the disintegration mechanism.

TABLE 7

| Binder | Particle size (μm) | Ø | Bulk density (g/cm³) | Tapped density (g/cm³) | Carr's Index | Moisture Content (%) | Friability (%) |
|---|---|---|---|---|---|---|---|
| Starch paste | 517.8 | 38.14 ± 0.32 | 0.699 ± 0.033 | 0.756 ± 0.011 | 7.66 ± 3.17 | 0.47% | 3.70 ± 1.6 |
| Sucrose | 526.9 | 34.59 ± 0.47 | 0.715 ± 0.034 | 0.784 ± 0.044 | 8.74 ± 1.46 | 0.10% | 2.22 ± 0.66 |
| DS 40% | 559.4 | 34.59 ± 0.47 | 0.688 ± 0.024 | 0.777 ± 0.031 | 11.46 ± 0.41 | 0.10% | 1.50 ± 0.82 |
| DS 50% | 563.4 | 34.93 ± 0.14 | 0.710 ± 0.036 | 0.784 ± 0.044 | 9.46 ± 0.48 | 0.20% | 1.25 ± 0.30 |
| DS 60% | 557.4 | 35.16 ± 0.63 | 0.652 ± 0.014 | 0.738 ± 0.011 | 11.58 ± 1.03 | 0.57% | 1.63 ± 0.22 |

The results of angle of repose, moisture content and bulk density are the means of three determinations
Ø = Angle of repose (mean ± S.D.)

Tablet Press:

A tablet press machine was used, EKO Laboratory Model Eccentric Press, to press flat tablets with a 10 ml radius with a tilted edge. Tablets weight ranges from 800-900 mg and contain 750 mg of both sodium bicarbonates and calcium carbonates each.

Evaluating Tablets:

Microscopic Electronic Scanning of Tablets:

The shape and structure of the tablets were examined using an electronic microscope (SEM). The obtained tablets were evaluated according to the 22nd American Pharmaceutical Constitution based on: weight symmetry, disintegration time, and friability test. A press strength test was done (toughness); characteristics of the calcium carbonate tablets prepared with different binders (Table 8).

All tablets met the requirements of the American Pharmaceutical Constitution according to the weight test. With regards to friability, calcium carbonates tablets pressed from granulation with date syrup gave acceptable friability values (less than 1%) while granules prepared with starch paste gave the tablets the most friability. Date syrup gave the tablets the most

TABLE 8

| Binder | Content moisture (%) | Hardness | Friability % | Disintegration (mint) |
|---|---|---|---|---|
| Starch paste | 0.63% | 5.05 ± 0.30 | f* | 17.00 ± 4.33 |
| Sucrose | 0.59% | 7.46 ± 0.40 | 8.12 ± 3.24 | 16.00 ± 1.09 |
| DS 40% | 0.40% | 9.58 ± 0.20 | 2.68 ± 1.75 | 5.11 ± 1.24 |
| DS 50% | 0.74% | 11.12 ± 1.34 | 0.80 ± 0.34 | 4.42 ± 0.63 |
| DS 60% | 0.46% | 11.44 ± 1.7 | 1.20 ± 0.45 | 4.76 ± 1.22 | f* = tablet is friable (few tablets were breakdown)

Characteristics of the Sodium Bicarbonates Tablets Pressed with Granules Prepared by Different Binders:

All tablets complied with the requirements of the American Pharmaceutical Constitution with regards to weight symmetry (Table 9). On the other hand, all tablets failed in complying with regards to friability except the ones granulized with date syrup 40%, which gave an acceptable value of less than 1%. Tablets granulized with date syrup 50% and 60% the least percentage of loss* and this is apparently because binders at this level of dilution were not able to give enough cohesion for the sodium bicarbonates granules and tablets. Tablets granulized with starch paste gave the highest loss percentage. Tablets granulized with starch paste have shown the least press strength (toughness) as indicated by the values of the press strength (toughness). All tablets gave a short disintegration time. Tablets granulized with starch paste gave the shortest disintegration time (less than 1 minute).

Tablet Sensation Tests:

Taste sensation tests were conducted on 7 volunteers (Table 10) by giving each tablet without any further information and were asked to chew each tablet on its own and to keep in their mouths for 15 seconds and then register the taste sensation of the tablet. Each volunteer would wash his mouth and gargle with water after each tasting and wait for 15 minutes.

TABLE 9

| Binder | Moisture Content (%) | Hardness | Friability | Disintegration |
|---|---|---|---|---|
| Starch paste | 0.47% | 3.22 ± .20 | f* | 0.88 ± 0.19 |
| Sucrose | 0.10% | 5.03 ± 0.30 | f* | 5.21 ± 1.68 |
| DS 40% | 0.10% | 8.19 ± 1.85 | 0.52 ± 0.1 | 3.79 ± 0.88 |
| DS 50% | 0.20% | 8.43 ± 1.72 | 1.89 ± 0.07 | 2.85 ± 0.61 |
| DS 60% | 0.57% | 7.52 ± 3.05 | 1.32 ± 0.49 | 3.08 ± 0.40 | f* = tablet is friable (few tablets were breakdown)

Naturally, sodium bicarbonates have a salty taste; calcium carbonates are without taste due to the water mixing values. Sodium bicarbonates tablets granulized with starch paste have a salty taste and no flavor; changing the binder to sucrose syrups decreased the salty taste but gave no flavor. Using date syrup as a binder produced tablets somewhat salty with a date flavor. These results are consistent with the results of the microscopic electronic scanning of the granules in which date syrup appeared similar to a granules painting substance adding a yellow color to the granules and tablets (FIG. 3). In the case of the calcium carbonates tablets, date syrup and sucrose syrup made the taste of tablets sweeter than when starch paste was used. In addition, date syrup as a binder gave tablets a date flavor. These results support the benefit of date syrup in masking the taste and giving an acceptable flavor.

TABLE 10

| Tablet | Binder | Flavor | Taste |
|---|---|---|---|
| Sodium bicarbonate | Starch (10%) | No | Salty |
|  | Sucrose (50%) | No | Less salty |
|  | Date syrup (50%) | Yes * | Slight salty |
| Calcium carbonate | Starch (10%) | No | no |
|  | Sucrose (50%) | No | Sweet |
|  | Date syrup (50%) | Yes * | Sweet |

* Meaning = date flavor

In general, date syrup was successful as a tablet binder for substances soluble in water and substances insoluble in water. At the same time, date syrup from different origins of the local dates will give similar results because the main components of date syrup and the reduced sugars and transformed sugars which make 60 to 65% of the weight do not change regardless of origin. Looking at the results obtained shows the range of benefit from local dates produced in the Kingdom of Saudi Arabia which are abundant which shows the possibility of benefit from the local produce in the preparation of tablets that have good qualities and are accepted by patients and benefiting from it in the Saudi Pharmaceutical Industry.

1—The use of date syrups with different concentrations (40, 50, 60%) as a tablet binder where it is used to granulize sodium bicarbonate powders as an example of substances soluble in water and calcium carbonates as an example of substances insoluble in water. The qualities of the obtained granules and tablets in comparison with other granules and tablets that use different kinds of binders such as starch paste 10% and sucrose syrup 50%. Date syrup has shown superiority as a tablet binder, and yielded excellent results. In addition, it gave the tablets good taste and a yellowish color.

2—The preparation of solutions, date syrup 40, 50, or 60%, sucrose syrup 50%, and starch paste 10%.

3—Elemental analysis of the date syrup with the use of an induction device to compare plasma and atomic rays.

4—Determining the specific gravity, viscosity, pH value of binder solutions, and determining the relation between the concentration of the date solutions and the viscosity.

5—The calcium bicarbonates and sodium carbonates solutions are assessed by the average size of the particle, apparent density, tapped density, and rest angle.

6—Preparing sodium bicarbonates and calcium carbonates using date syrup solutions, starch paste solutions, and sucrose syrup solutions.

7—Study of the shape and structure (morphology) of the granules and tablets of sodium bicarbonates and calcium carbonates prepared with different binders using an electronic microscope.

8—The obtained granules of sodium bicarbonates and calcium carbonates will be evaluated according to: the average size of a particle, strength of the particle, apparent density, tapped density, and rest angle.

9—Manufacturing tablets of the prepared granules with different agglutinants using the tablet machine.

10—Evaluation and study of the produced tablets, according to the American Pharmaceutical Constitution, article 22, according to: weight symmetry, time of disintegration, friability test and carrying out a pressure strength test (hardness). Results have shown superiority of the date drink 11—Testing taste and flavor on a sample of volunteers; date syrup has shown superiority in masking the taste and introducing a good flavor to the tablets.

The features of the present invention disclosed in the specification, the claims and/or in the accompanying drawings, may, both separately, and in any combination thereof, be material for realizing the invention in various forms thereof.

The invention claimed is:

1. A method for producing a composition wherein the method comprises the use of an agglutinant for granulation of water-soluble substances and water-insoluble substances, wherein the agglutinant consists essentially of a date syrup having only soluble date components.

2. The method according to claim 1, used to manufacture a solid dosage form.

3. The method according to claim 1, wherein said date syrup is used at a concentration in the range of from 40% to 60% (w/w date syrup:water).

4. The method according to claim 1, wherein the agglutinant is an agglutinant for a solid dosage form selected from tablets, pills, lozenges, capsules, suppositories, powders, and granules.

5. The method according to claim 1, wherein said date syrup is used as agglutinant in an agglutinant solution, and wherein the specific gravity is 0.8-1.3 g/ml, and/or the viscosity is 4-20 cP, and/or the pH value is in a range of from 3-5.

6. The method according to claim 1, wherein said water-soluble substances and said water-insoluble substances are assessed by their average molecular size, apparent density, pitting density and rest angle.

7. The method according to claim 4, wherein said water-soluble substances and water-insoluble substances are granulized separately using date syrup as tablet agglutinants to prepare solid dosage form granules and tablets.

8. The method according to claim 7, wherein the shape and structure of the granules and tablets of said water-soluble and water-insoluble substances prepared are studied using an electron microscope in order to differentiate and obtain granules and tablets based on their average molecular size, strength of molecule, apparent density, pitting density and rest angle.

9. The method according to claim 1, wherein tablets are manufactured from the granules prepared, using a tablet machine.

10. The method according to claim 9, wherein the manufactured tablets are assessed and studied according to the American Pharmaceutical Constitution, Article 22, in relation to weight symmetry, time of disintegration, fragility test, and hardness test.

11. The method according to claim 1, wherein the taste and flavor of the tablets manufactured is tested on a sample of volunteers.

12. A solid dosage form, comprising an agglutinant, wherein the agglutinant consists essentially of date syrup having only soluble date components.

13. The dosage form according to claim 12, selected from the group comprising tablets, pills, lozenges, capsules, suppositories, powders and granules.

14. The dosage form comprising date syrup as an agglutinant, wherein said dosage form has been prepared using the method in accordance with claim 1.

15. The method, according to claim 1, wherein the water-soluble substance is sodium bicarbonate.

16. The method, according to claim 1, wherein the water-insoluble substance is calcium carbonate.

17. The method, according to claim 5, wherein the pH is 4.5.

18. The method, according to claim 1, further comprising the step of adding at least one additional ingredient selected from the group consisting of: lubricants, agents influencing release profile, binder substances and humectants.

* * * * *

UNITED STATES PATENT AND TRADEMARK OFFICE
CERTIFICATE OF CORRECTION

PATENT NO. : 8,647,674 B2  Page 1 of 1
APPLICATION NO. : 13/259725
DATED : February 11, 2014
INVENTOR(S) : Alanazi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 53 days.

Signed and Sealed this

Twenty-ninth Day of September, 2015

Michelle K. Lee
*Director of the United States Patent and Trademark Office*